United States Patent [19]

Moen et al.

[11] 4,078,896
[45] Mar. 14, 1978

[54] PHOTOMETRIC ANALYZER

[75] Inventors: Art M. D. Moen, Covina; James R. Robison, La Mirada, both of Canada

[73] Assignee: International Telephone and Telegraph Corporation, New York, N.Y.

[21] Appl. No.: 761,547

[22] Filed: Jan. 21, 1977

[51] Int. Cl.² .................... G01J 3/48; G01N 21/28
[52] U.S. Cl. ............................. 23/254 R; 356/188
[58] Field of Search .................... 23/254 R, 232 R; 356/186, 188, 189

[56] References Cited

U.S. PATENT DOCUMENTS

| 3,718,429 | 2/1973 | Williamson Jr. | 23/232 R |
|---|---|---|---|
| 3,796,887 | 3/1974 | Vincent et al. | 356/207 X |
| 3,882,028 | 5/1975 | Zolner | 23/254 R X |
| 4,015,479 | 4/1977 | Apple | 23/232 R X |

*Primary Examiner*—Robert M. Reese
*Attorney, Agent, or Firm*—A. Donald Stolzy

[57] ABSTRACT

A photometric analyzer to monitor one or more constituents of a mixture, such as by producing indications of the concentrations of sulfur dioxide and NOX (NO + NO$_2$) in flue gases. The NO is converted to detectable NO$_2$ by ozone thus:

$$NO + O_3 \rightarrow NO_2 + O_2$$

Contrary to accepted theory, the following reaction to undetectable N$_2$O$_5$ is negligible because of the rapid flow of flue gas:

$$NO_2 + O_3 \rightarrow N_2O_5 + O_2$$

21 Claims, 21 Drawing Figures

PHOTOMETRIC ANALYZER

BACKGROUND OF THE INVENTION

This invention relates to devices for producing output signals directly proportional to the concentration of the constituent of a mixture, and more particularly to a photosensitive measuring system.

A photometric device is described herein for the analysis of flue or stack emissions. Most of the pollutant gases found in stack emissions absorb either ultraviolet or visible light, and from the amount of light absorbed, the concentration of the gas can be determined. The device of the present invention may be similar to the type disclosed in U.S. Pat. No. 3,796,887 issued Mar. 12, 1974.

It is known in the art that:

$$NO + O_3 \rightarrow NO_2 + O_2 \quad (1)$$

and $$NO_2 + O_3 \rightarrow N_2O_5 + O_2. \quad (2)$$

See U.S. Pat. No. 3,718,429 issued Feb. 27, 1973. However, $N_2O_5$ is not detectable.

SUMMARY OF THE INVENTION

The photometer described in this disclosure overcomes the above-described and other difficulties by utilizing an optical path length within a perforate probe previously placed inside the stack, effecting the reaction of equation (1) by passing ozone through a separate perforate tube inside the probe, and measuring gas concentration in the stack environment.

The instrument of the present invention can be used in ways not disclosed herein or for measuring the concentration of any one, two, three or more gaseous substances which absorb light in the visible or ultraviolet regions of the spectrum. Such gases include, for example, $SO_2$, NO, $NO_2$ and $H_2S$. It can, therefore, be used to monitor emissions from power boilers and recovery furnaces. Being able to measure both sulfur dixoide and hydrogen sulfide simultaneously, it can be used for process control in the Claus sulfur recovery process. The instrument also can be used to measure the parameters relating to smoke density and turbidity. The instrument of the present invention may also be used to analyze pollutants which absorb in the infrared regions of the spectrum.

The reaction of equation (2) is minimized or eliminated due to the high velocity of flue gases.

The above-described and other advantages of the present invention will be better understood from the following detailed description when considered in connection with the accompanying drawings.

BRIEF DESCRIPTION OF THE DRAWINGS

In the drawings, which are to be regarded merely as illustrative.

DESCRIPTION OF THE PREFERRED EMBODIMENT

Figure 1:
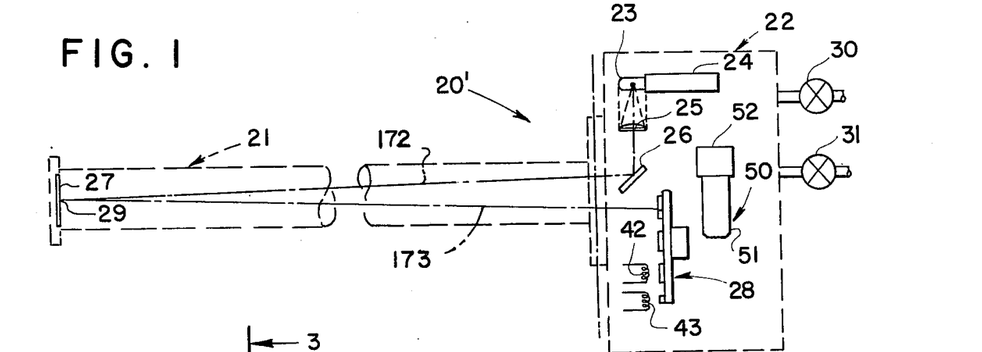
FIG. 1 is a diagrammatic view of a photometric analyzer constructed in accordance with the present invention.

In FIG. 1, a photometric analyzer shown constructed in accordance with the present invention is indicated at 20' including a probe 21, and a housing 22 fixed relative to and contiguous to probe 21.

A mercury lamp 23, having a base 24, is fixed relative to housing 22 inside thereof. A collimator lens 25 collimates the light which emanates from the lamp 23. This light is then reflected off of a mirror 26 to a mirror 27 fixed relative to probe 21 at the left end thereof, as viewed in FIG. 1. The light reflected from mirror 26 is then reflected back toward a wheel 28 from a point 29 on mirror 27.

As will be explained, valves may be provided at 30 and 31 to admit air under pressure to probe 21 for two purposes. One purpose is to provide an "air curtain" at each end of probe 21 contiguous to windows therein, not shown in FIG. 1, to keep the windows clean.

Air may also be applied to purge the probe 21 of any gas except air periodically for calibration purposes, as will be described.

Ozone is released in probe 21 as will be described.

Typically, valve 30 may be turned on to establish the air curtain at each window. Valve 31 may be turned on to purge the probe 21 with air.

Figure 2:
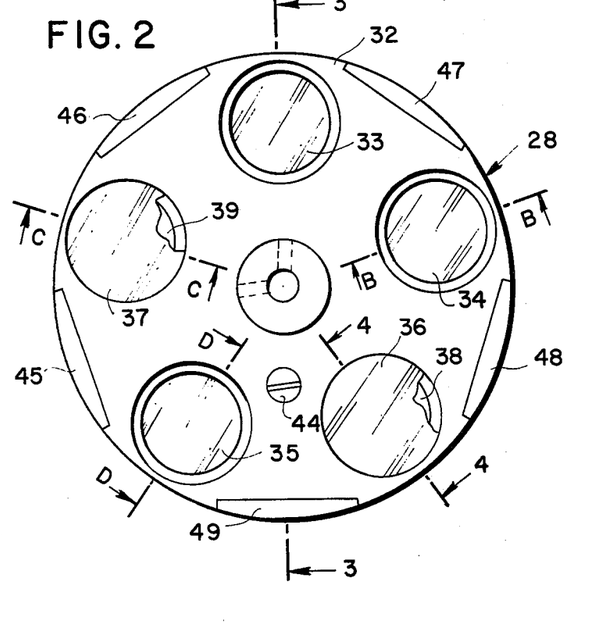
FIG. 2 is a front elevational view of a rotatable wheel shown in FIG. 1.

As shown in FIG. 2, wheel 28 includes a disc 32 which has filters 33, 34 and 35 fixed thereto. Wheel 28 also has neutral density filters 36 and 37 fixed thereto. A sectional view taken on the line 3—3 would appear as in FIG. 3. However, sectional views taken on the lines B—B and D—D would also be identical to the view of FIG. 3.

Figure 4:
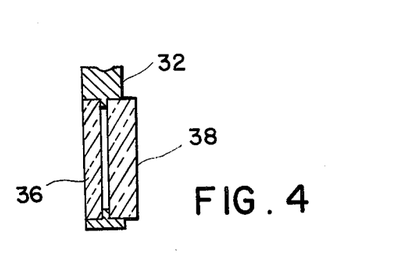
FIG. 4 is a sectional view of a portion of the wheel taken on the line 4—4 shown in FIG. 2.

A filter 38 is fixed to disc 32 as indicated in FIG. 4 adjacent neutral density filter 36. A section taken on the line C—C in FIG. 2 would be identical to that shown in FIG. 4. Another filter 39 is thus positioned adjacent neutral density filter 37.

The photometric analyzer 20 is employed to detect $SO_2$ and/or $NO_2$ and/or NO in flue gases. For this purpose, filter 33 may be described as a reference filter having an effective wavelength of 546 nanometers. Filter 34 may be described as the $SO_2$ measuring filter with an effective wavelength of 313 nanometers.

Filter 38 may be described as the $SO_2$ calibrate filter, and may have an effective wavelength of 313 nanometers.

Filter 35 may be described as the $NO_2$ measuring filter and may have an effective wavelength of 435 nanometers. However, NO is converted to $NO_2$ thus: $NO + O_3 \rightarrow NO_2 + O_2$.

Filter 39 may be described as the $NO_2$ calibrate filter, and have an effective wavelength of 435 nanometers. Again, NO is converted to $NO_2$.

It will be noted that filters 33, 34, 35, 38 and 39 have centers which lie on a mathematical circular cylinder concentric with the axis of rotation of wheel 28.

Although this invention is by no means limited to measuring the concentration of $SO_2$ and/or $NO_2$ and/or NO, for the purposes herein, both neutral density filters 36 and 37 may transmit the same portion of all wavelengths of light. This portion is perferably 1/1000 of light which illuminates each.

Figure 3:
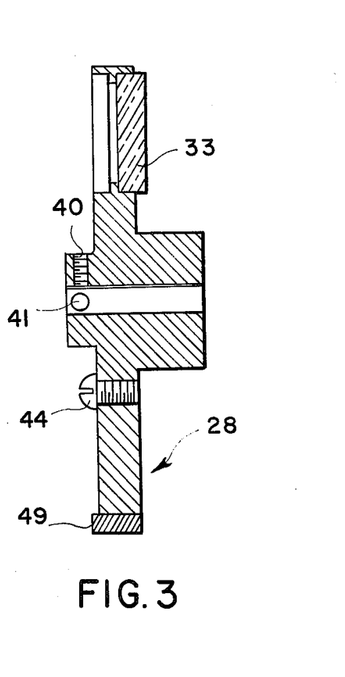
FIG. 3 is a vertical sectional view through the wheel taken on the line 3—3, shown in FIG. 2.

As shown in FIG. 3, threaded set screw holes are provided at 40 and 41 for fixing wheel 28 to a drive shaft. The drive shaft is driven by a motor at a constant speed, although this is not critical.

As shown in FIG. 1, magnetic pickups are provided at 42 and 43. A voltage pulse is induced in pickup 42 when a ferromagnetic screw 44 passes by it, as shown in FIGS. 2 and 3.

Wheel 28 has ferromagnetic slugs 45, 46, 47 and 48 fixed thereto, as shown in FIG. 2. When the slugs pass pickup 43, a voltage pulse is, each time, induced in pickup 43. A slug is provided at 49 which is made of stainless steel and is used as a counterbalance. All of the slugs shown in FIG. 2 are equally spaced. The same is true of the filters. The filters are also positioned midway between each immediately adjacent pair of slugs.

In FIG. 1, when wheel 28 turns, each filter in succession is passed through the light beam from mirror 27. Whatever is passed by each filter or combination of filters is then received by a photomultiplier 50, shown in FIG. 1.

Figure 5:
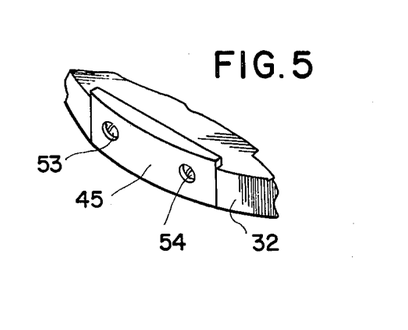
FIG. 5 is a broken away perspective view of a portion of the wheel shown in FIG. 2.

Each of the slugs shown in FIG. 2 is fixed relative to disc 32 by a pair of corresponding screws 53 and 54, as shown in FIG. 5. In FIG. 5, slug 45 is shown by way of example.

Figure 6:
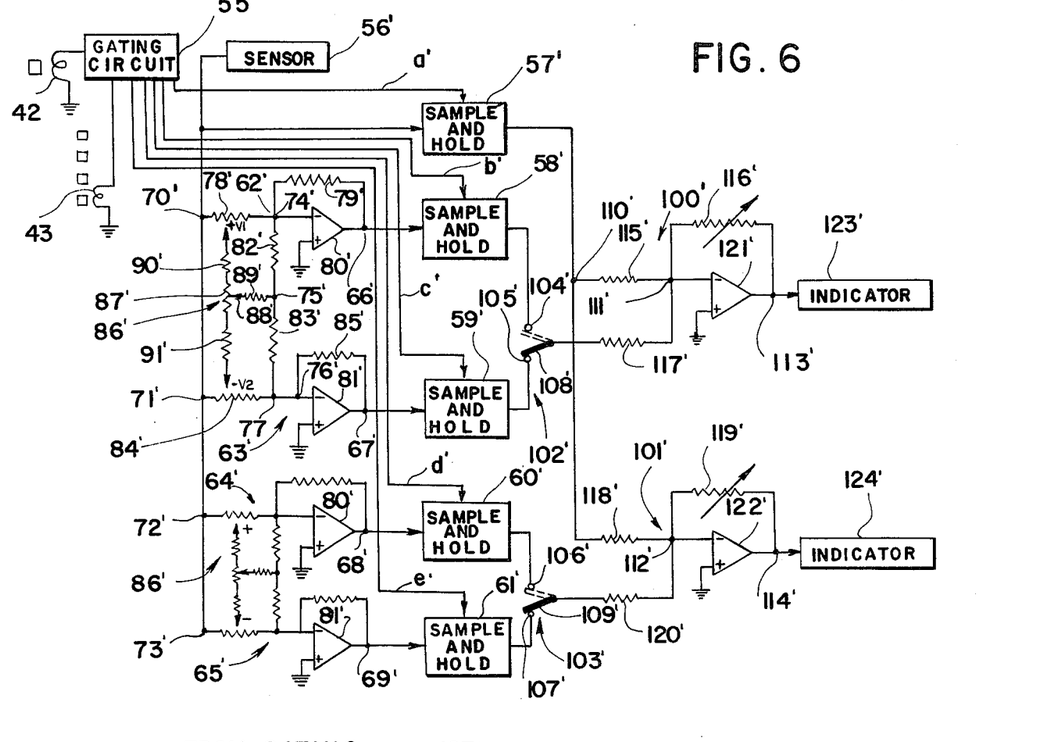
FIG. 6 is a diagrammatic view of the electrical portion of the analyzer.

In FIG. 6, pickups 42 and 43 are shown connected to a gating circuit 55'.

Also shown in FIG. 6 are sample and hold circuit 57', 58', 59', 60' and 61'.

Also shown in FIG. 6 is a sensor 56' which is connected to one input of sample and hold circuit 57' and to the inputs of analog adders 62', 63', 64' and 65'. The outputs of adders 62'-65' are taken at junctions 66', 67', 68' and 69', respectively. The outputs at junctions 66'-69' are inverted from the inputs at junctions 70', 71', 72' and 73', respectively. Analog adders 62'-65' provide for zeroing, as will be described.

Adders 62' and 63' are respectively substantially identical to adders 64' and 65', respectively. Adders 64' and 65' will, therefore, not be described in detail.

All of the input junctions 70'-73' are connected from the output of sensor 56'. Adder 62' has junctions at 74' and 75'. Junction 75' is also a common junction of adder 63' because the same constant voltage is added or substracted in the case of both adder 62' and adder 63'. Adder 63' includes a junction at 77'.

Adder 62' includes a resistor 78' connected between junctions 70' and 74'. A feedback resistor 79' is connected between junctions 74' and 66'. Junction 66' is connected to an input to sample and hold circuit 58'. Junction 74' is connected to the inverting input of amplifier 80'. Similarly, adder 63' includes an amplifier 81'. A resistor 82' is connected between junctions 74' and 75'. A resistor 83' is connected between junctions 75' and 77'. A resistor 84' is connected between junctions 71' and 77'. A feedback resistor 85' is connected between junctions 76' and 67'. Junctions 77' and 76' are connected together and to the inverting input of amplifier 81'. The non-inverting input of amplifiers 80' and 81' are connected to ground.

A potentiometer is provided at 86' having a winding 87', and a wiper 88'. A resistor 89' is connected between wiper 88' and junction 75'. A resistor 90' is connected from the upper end of winding 87' to a potential $+V1$. A resistor 91' is connected from the lower end of potentiometer winding 87' to a potential $-V2$.

Gating circuit 55' has output leads $a'$, $b'$, $c'$, $d'$ and $e'$ connected respectively to circuits 57'-61'.

Another pair of analog adders are provided at 100' and 101'. Single-pole, double-throw switches are provided at 102' and 103'. Switch 102' has a contact 104' connected from the output of circuit 58'. Switch 102' has a contact 105' connected from the output of circuit 59'. Switch 103' has a contact 106' connected from the output of circuit 60'. Switch 103' has a contact 107' connected from the output of circuit 61'. Switches 102' and 103' have poles 108' and 109', respectively. A junction is provided at 110' connected from the output of circuit 57'. Junctions are provided at 111', 112', 113' and 114'.

A resistor 115' is connected between junctions 110' and 111'. A variable feedback resistor 116' is connected between junctions 111' and 113'. A resistor 117' is connected between pole 108' and junction 111'. A resistor 118' is connected between junction 110' and junction 112'. A feedback resistor 119' is connected between junctions 112' and 114'. A resistor 120' is connected between switch pole 109' and junction 112'. A differential amplifier 121' has an inverting input connected from junction 111' and an output connected to junction 113'. A differential amplifier 122' has an inverting input connected from junction 112' and an output connected to junction 114'. Both of the noninverting inputs of amplifier 121' and 122' are connected to ground. An indicator 123' is connected from junction 113'. An indicator 124' is connected from junction 114'.

Sensor 56' may include the photomultiplier 50 and the circuit therefor. Both the photomulipler and the circuit are entirely conventional. Moreover, it is conventional to operate a photomultiplier to give a D.C. output voltage which is equal to the common logarithm of the input thereto.

Indicator 123' may simply be a voltmeter calibrated in concentration (e.g. volume per unit volume). Alternatively, indicator 123' may be a recording voltmeter. Indicator 124' may or may not be identical to indicator 123', as desired.

Figure 7:
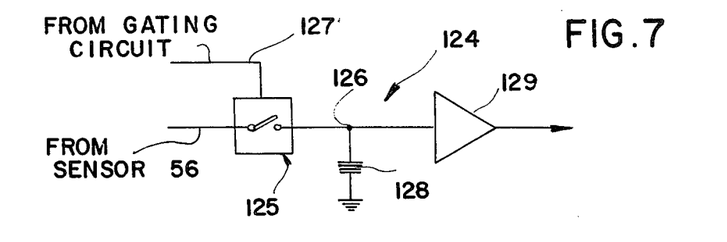
FIG. 7 is a diagrammatic view of a sample and hold circuit, five of which are shown in FIG. 6.

Each sample and hold circuit shown in FIG. 6 may be identical to a sample and hold circuit 124, shown in FIG. 7, including a sampling switch 125 connected from sensor 56 to a junction 126. The time that switch 125 is closed is determined by the pulse width at one of the outputs $a'$, $b'$, $c'$, $d'$, $e'$ shown in FIG. 6.

Figure 8:
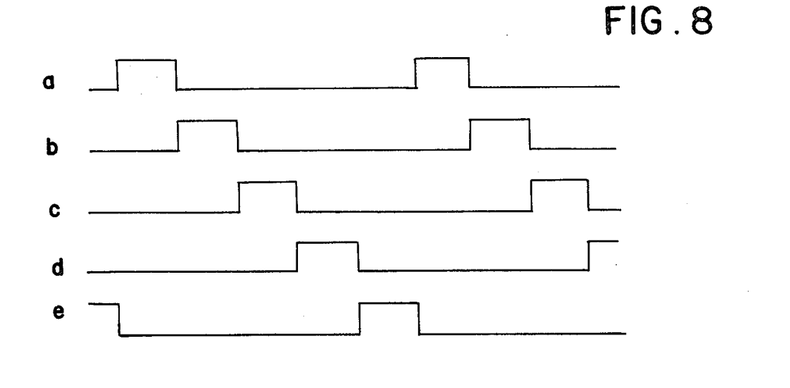
FIG. 8 is a graph of a group of waveforms characteristic of the operation of a gating circuit shown in FIG. 6.

Pulses are supplied to switch 125 of one of the types shown in FIG. 8 over lead 127. Thus, the gating circuit 55' outputs at $a'$ through $e'$ are respectively indicated at $a$, $b$, $c$, $d$ and $e$ in FIG. 8.

Note will be taken in FIG. 8 that each of the pulse trains $a$, $b$, $c$, $d$ and $e$ utilize sets of pulses, the pulses of each set having a constant width for each set. The pulse repetition frequency is also the same throughout the waveforms of FIG. 8. Only the phase has been changed. Note will be taken that one pulse begins at the termination of a preceding pulse. The pulse width is equal to one-fifth of the pulse period. For a complete description of gating circuit 55', see the said U.S. Pat. No. 3,796,887 issued Mar. 12, 1974.

Figures 9, 10:
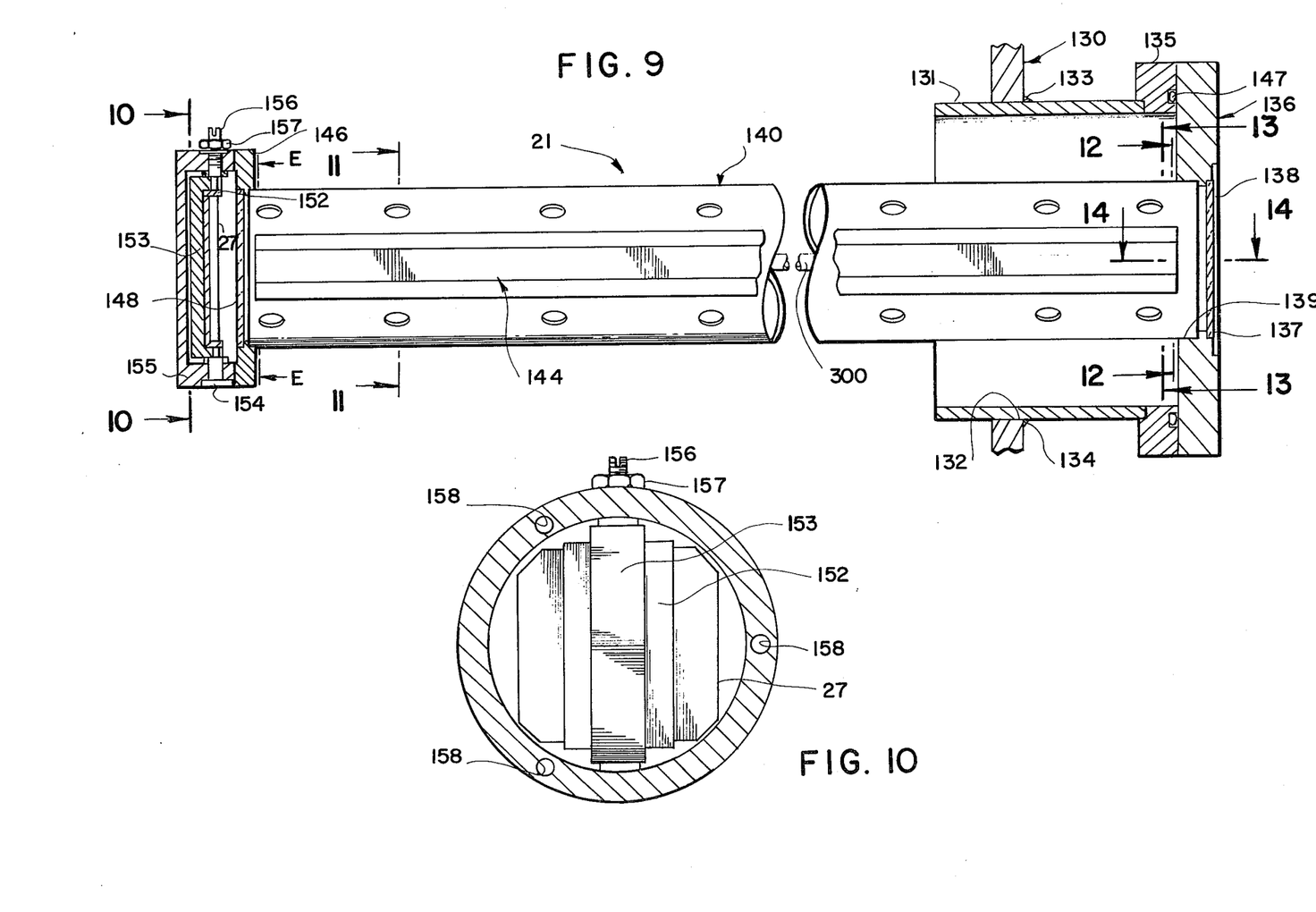
FIG. 9 is a side elevational view, partly in section, of a probe for mounting inside a flue or stack.
FIG. 10 is a transverse sectional view of the probe taken on the line 10—10, shown in FIG. 9.

Probe 21 is illustrated in greater detail in FIG. 9. A plate 130 represents the wall of a flue. A mounting cylinder 131 is fixed in a bore 132 of plate 130 by welding at 133 and 134.

A ring 135 is fixed to cylinder 131 by welding or otherwise, not shown. A plate 136 is preferably bolted to ring 135, in assembly, by bolts, not shown. Plate 136 is fixed to housing 22, shown in FIGS. 1 and 15.

Plate 136 in FIG. 9 has an annular groove 137 therein in which a transparent window 138 is fixed. Plate 136 also has a groove 139 in which a hollow cylindrical tube 140 is fixed.

Figure 11:
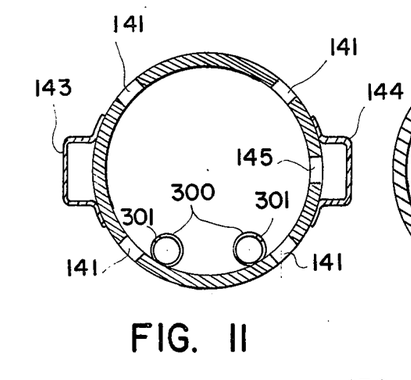
FIG. 11 is a transverse sectional view of the probe taken on the line 11—11, shown in FIG. 9.
Figure 12:
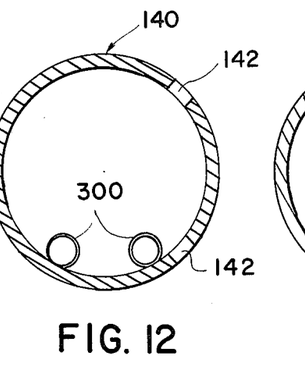
FIGS. 12 and 13 are additional transverse sectional views through the probe taken on the lines 12—12 and 13—13, respectively, shown in FIG. 9.

Tube 140 has four symmetrical holes therethrough at 141 which are located at uniformly spaced axial intervals. Holes are also provided at opposite ends, as indicated at 142 in FIG. 12. Holes 141 are shown again in FIG. 11. Also shown in FIG. 11 are two hat-shaped sections 143 and 144. Section 144 covers a row of holes 145. Air is thus supplied to the interior of section 144 for purging probe 21 with air. Hat-shaped section 144 is closed at its left end, as viewed in FIG. 9. However, this closure cannot be seen because a portion of a ring 146 has been removed due to the section taken.

At its right end, section 144, as shown in FIG. 9, may be sealed except for a tube inserted thereinto out of which air under pressure can flow down section 144 therewith into the interior of tube 140 through the row of holes 145. See FIG. 11. Holes 145 may have a lengthwise spacing identical to the holes 141, if desired.

As shown in FIG. 9, if desired, an O-ring seal 147 may be provided between plate 136 and ring 135.

Figure 13:
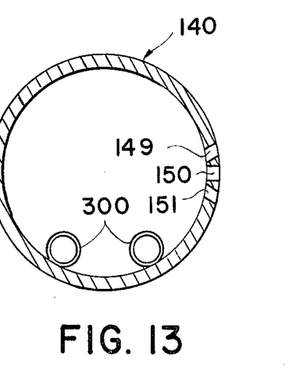

Section 143, shown in FIG. 11, is employed to provide the air curtain at opposite ends of the tube 140. The window opposite window 138 is fixed in ring 146 at 148. The air curtains are provided because there are no holes between hat-shaped section 143, as shown in FIG. 11, except at the ends thereof indicated at 149, 150 and 151 in tube 140 as shown in FIG. 13. The view of FIG. 13 would be the same if taken on the line E—E, shown in FIG. 9 except for a tube 300 through which ozone flows and is dispensed inside tube 140.

Mirror 27 is again shown in FIGS. 9 and 10 fixed to a bracket 152 that is fixed to a yoke 153. Yoke 153 is fixed to a pin 154 rotatable in a bracket 155. Mirror 27 is rotatable by adjustment of a screw 156 which has a lock nut 157 thereon.

Screws, not shown, are slidable through holes 158 through bracket 155 and are threaded into ring 146.

Figure 14:
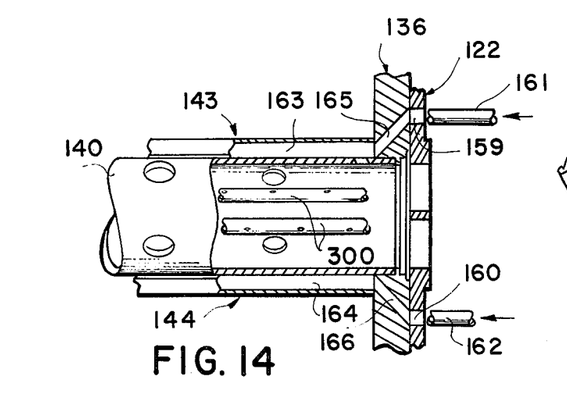
FIG. 14 is a longitudinal view, partly in section, of the probe shown in FIG. 9, and taken on the line 14—14 therein.

Housing 22, shown in FIG. 14, has openings 159 and 160 through which air may pass for providing the air curtains and purging, respectively. If desired, air inlet tubes 161 and 162 may be sealed in openings 159 and 160, respectively. Sections 143 and 144 form passages 163 and 164, respectively, with tube 140.

Passage 163 is connected from opening 159 by a hole 165 through plate 136. Similarly, passage 164 is connected to opening 160 by a hole 166. If desired, holes 165 and 166 may be identical in size and shape. They also may be substantially cylindrical having their axes lying in a plane through the axis of tube 140. The holes 165 and 166 may be, if desired, 45° holes.

Ozone tube 300 may have end portions exiting tube 140 in the same manner as through holes 165 and 166, but 90° around tube 140 and through tube 140 itself, or in any conventional manner.

Figure 15:
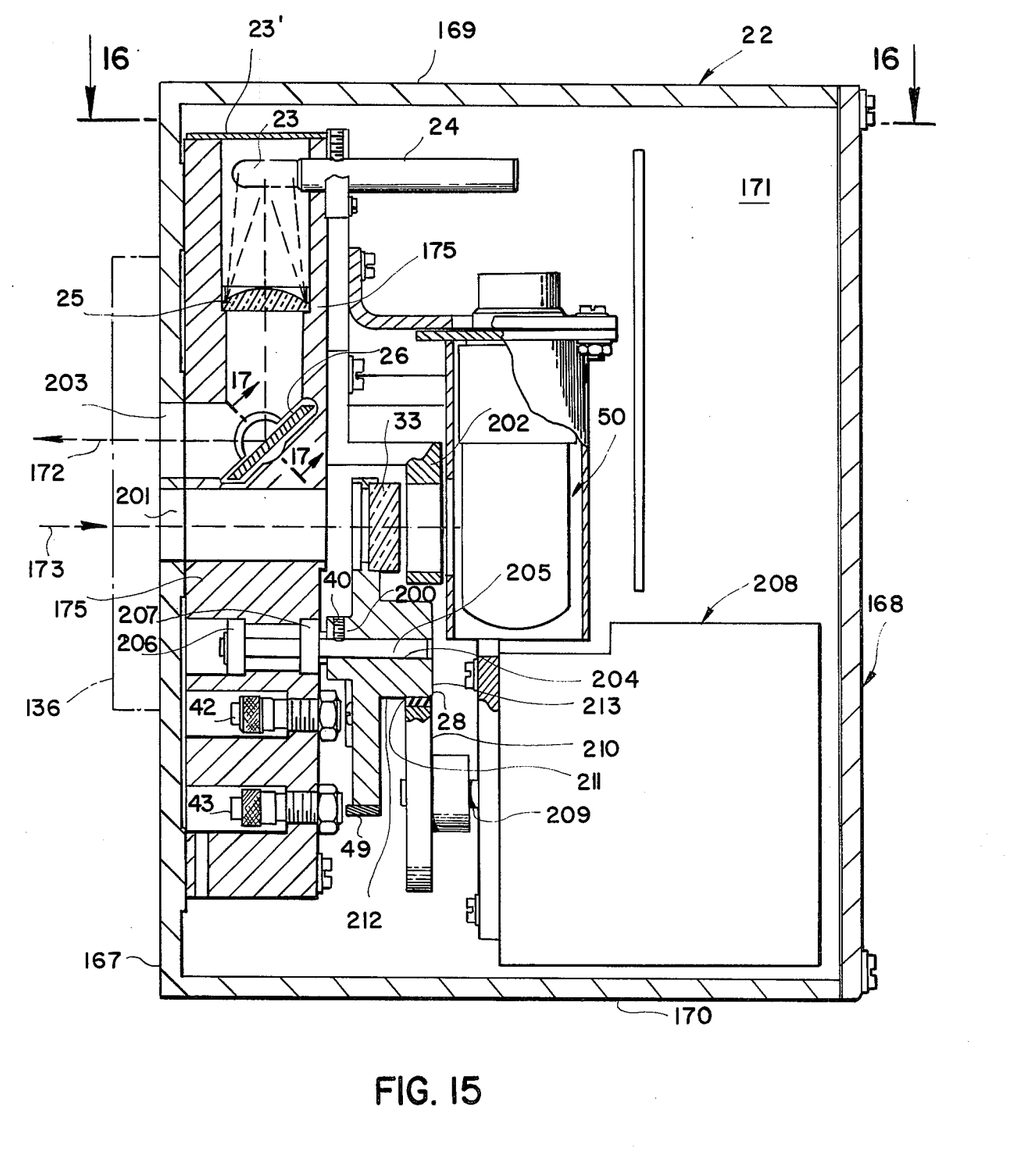
FIG. 15 is a vertical sectional view through a housing which is fixed contiguous to the probe.

In FIG. 15, housing 22 includes front and rear panels 167 and 168, respectively. Housing 22 also includes top and bottom panels 169 and 170, respectively. Housing 22 also includes two side panels 171 and 171', respectively, only one of which is shown in FIG. 15. All of the panels 167–171 and 171' are fixed relative to each other by any conventional means. They preferably form a generally rectangular box. The box is preferably light tight. In this regard, in FIG. 9, a perforate tube may be provided spaced from, but concentric with, tube 140 with apertures staggered relative to apertures 141 to prevent light inside the stack from entering photomultiplier 50, shown in both of FIGS. 1 and 15.

Lamp 23, lens 25 and mirror 26 are again shown in FIG. 15. Due to the fact that the view of FIG. 15 is greatly enlarged over that portion of the apparatus shown in housing 22 in FIG. 1, lines 172 and 173 showing a single central ray of light appear to be parallel. This is true because the angle that these lines make with respect to each other is very small. The perpendicular distance between lines 172 and 173 is quite small in comparison to the distance that mirror 27 is from mirror 26 in FIG. 1. Note lines 172 and 173 in FIG. 1. The angle that they make may be about 1 degree. If desired, FIGS. 2, 3, 4 and 9–17 may be considered full scale drawings.

Figure 17:
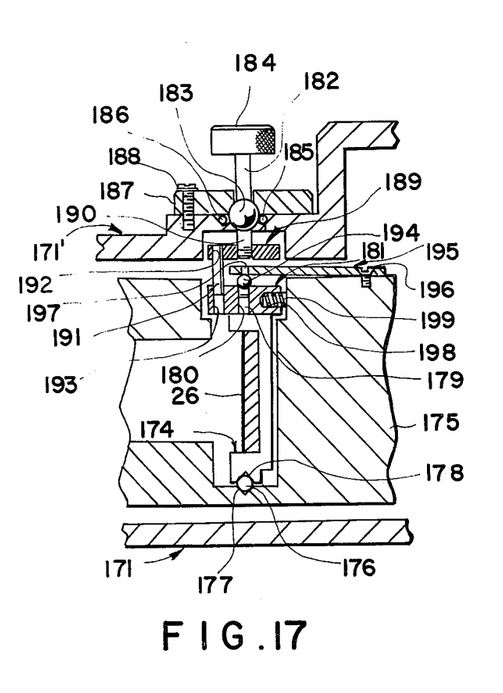
FIG. 17 is a sectional view taken on the line 17—17, shown in FIG. 15.

Mirror 26 is mounted as shown in FIG. 17 is an arrangement which is equivalent to gimbals. Mirror 26 is fixed to a bracket 174.

A supporting structure 175 is fixed relative to housing 22 inside thereof in FIG. 17. Bracket 174 is rotatable on a ball 176 which fits in a groove 177 in structure 175 and a groove 178 in bracket 174.

Bracket 174 also has a pin 179 fixed rigidly therewith that is press fit in a hole 180 in a connecting part 181. Pin 179 is thus fixed rigidly with respect to part 181.

As shown in FIG. 17, an adjustment shaft 182 is fixed to a ball 183 which is rotatable to a limited extent about its center in any direction. Shaft 182 has a knurled knob 184 fixed to its upper end. Panel 171' has a groove 185 therein in which an O-ring 186 is trapped by a plate 187 that is fixed to the outer surface of side panel 171' by three cap screws 188, only one of which is shown in FIG. 17 for clarity.

Another stub shaft 190 is fixed to the lower end of ball 183. A disc 189 is fixed to the end of shaft 190. A pin 191 is press fit through a hole 192 in disc 189 and is thereby fixed relative thereto. Pin 191 extends into a hole 193 that goes all the way through part 181. Pin 191 is slidable in hole 193 to permit some movement of the parts when ball 183 is rotated about an axis through its center perpendicular to the drawing of FIG. 17.

Hole 180 in part 181 goes all the way through part 181. A ball 194 covers the upper end of hole 180 and acts as a pivot for part 181. A leaf spring 195 is fixed to structure 175 by two screws 196, only one of which is shown in FIG. 17. Leaf spring 195 has a hole 197, the lower end of which is covered by ball 194.

Part 181 has a recess 198 therein in which a helically coiled spring 199 is located to bias part 181 on the, more or less, right-hand surface of pin 191, as shown in FIG. 17.

Light entering the housing 22 in the direction of line 173 in FIGS. 1 and 15 then passes through one of the filters 33, 34 and 35 (FIG. 2), or through both of the filters 36 and 38 or through both of the filters 37 and 39.

Although wheel 28 rotates continuously at a substantially constant angular velocity, one of its positions during the rotation thereof is indicated again in FIG. 15. Wheel 28 is shown with filter 33. Light can thus pass to photomultiplier 50 by entering a cylindrical opening 201 in housing 22 through front panel 167, passing through filter 33 and through a filter stop 202.

Light traveling in the direction of line 172 exits through a cylindrical opening 203 in housing 22. Wheel 28 has a central cylindrical bore 204 through which a cylindrical shaft 205 projects, wheel 28 being fixed to shaft 205 by two set screws 200 in the respective threaded holes 40 and 41, shown in FIG. 3. Shaft 205 is maintained in a fixed axial, but rotatable, position in conventional bearings 206 and 207 which are, in turn, fixed in structure 175.

A conventional electric motor 208 is provided with an output shaft 209 fixed to a driving disc 210. A layer of rubber is bonded at 211 to the periphery of disc 210. Wheel 28 and motor 208 are then mounted in positions such that layer 211 provides a friction drive for wheel 28 on a cylindrical portion 212 of a hub 213 of wheel 28. Pickups 42 and 43, which may be entirely conventional, are again indicated in FIG. 15.

In FIG. 15, slugs 47 and 48 are omitted due to the section taken. Slug 46 has been omitted for clarity.

Figure 16:
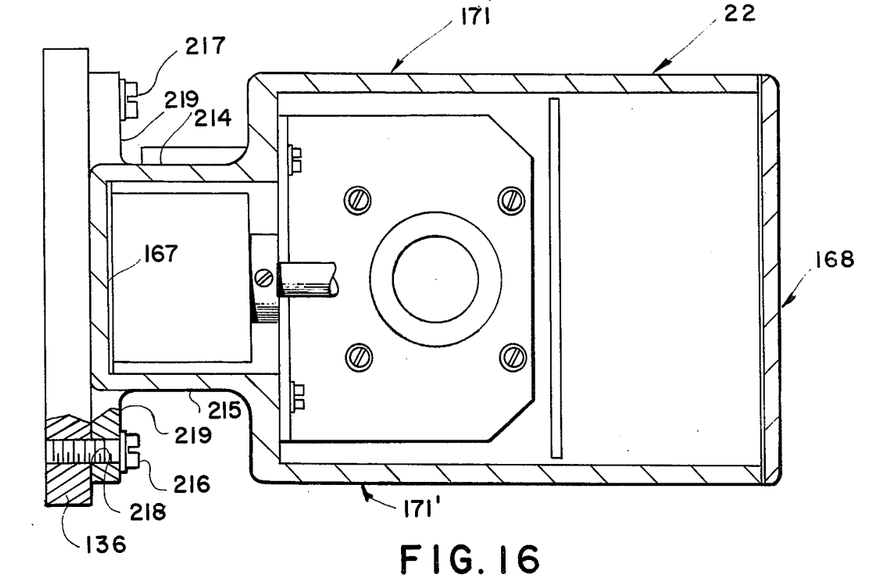
FIG. 16 is a transverse sectional view taken on the line 16—16, shown in FIG. 15.

As shown in FIG. 16, if desired, side panels 171 and 171' may have necked down portions 214 and 215, respectively.

Also, as shown in FIG. 16, plate 136 is fixed relative to housing 22 by cap screws 216 and 217 which are threaded to plate 136 and extend through corresponding holes 218 in ears 219 fixed to opposite sides of side panels 171 and 171', respectively.

Figure 18:
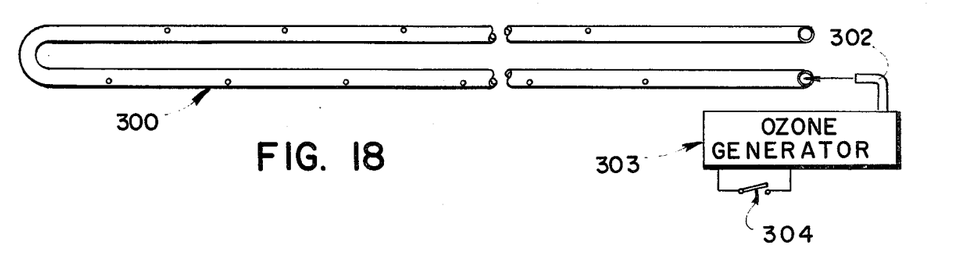
FIG. 18 is a top plan view of an ozone generator and ozone distribution tube.
Figure 19:
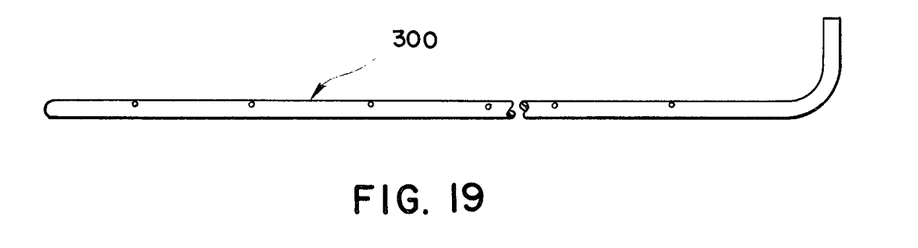
FIG. 19 is a side elevational view of the tube shown in FIG. 18.
Figure 20:
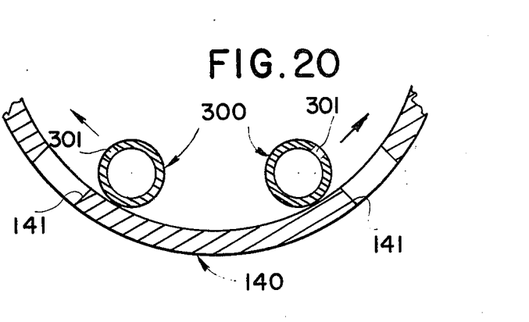
FIG. 20 is an enlarged, broken away transverse sectional view of the probe and ozone distribution tube taken on the line 20—20, shown in FIG. 18.

In FIGS. 18, 19 and 20 holes are provided at 301 to blow ozone over holes 141. In FIG. 18, output tube 302 of a conventional ozone generator 303 is sealed to tube 300. Generator 303 is turned on and off by a switch 304.

Figure 21:
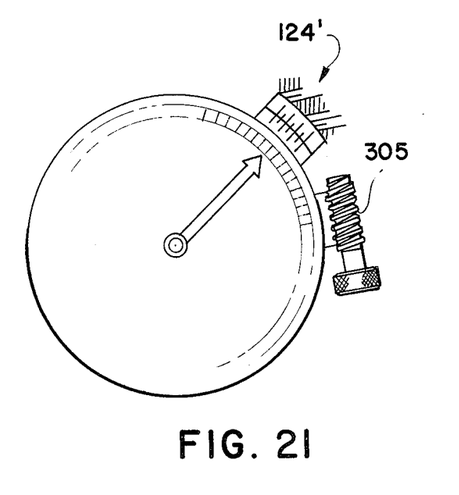
FIG. 21 is an elevational view of an indicator.

Indicator 124' in FIG. 6 is shown again in FIG. 21. A worm 305 adjusts the zero for $NO_2$ [no equation (1) reaction]. Switch 304 (FIG. 18) is opened in this case. To obtain NO and $NO_2$, switch 304 is closed.

All the structures herein except 140, 300, 301, 302, 303, 304, 305 and those of FIG. 21 may be identical to corresponding ones in U.S. Pat. No. 3,796,887 issued Mar. 12, 1974, if desired.

OPERATION

The embodiment of the present invention disclosed herein provides an indication, recorded or not, of the concentrations of $SO_2$, NO and $NO_2$ in stack gases.

A feature of the present invention resides in the use of time-shared reference-measure-calibrate arrangements where the selfsame optical path is selected for not only the reference filter, but also the measuring filter and the calibration filter for gas being monitored. Moreover, a single reference filter may be used in producing an indication of the concentration of more than one gas. For example, not only two, but three or more gases may be monitored at the same time.

During the operation of the photometric analyzer 20, shown in FIG. 1, lamp 23 provides light, which light is collimated by lens 25 and reflected by mirror 26 toward mirror 27. The light thus is transmitted through the interior of the tube 140, shown in FIG. 9, through gases in tube 140 along the line 172, shown in FIG. 1. After it reaches the mirror 27, shown in FIG. 1, the light is reflected along the line 173 back through the gases inside tube 140.

The transmission of light along lines 172 and 173 results in light of some wavelengths according to the absorption spectra of $SO_2$ and/or $NO_2$ being attenuated. It is, by knowing the absorption spectra of $SO_2$ and/or $NO_2$, possible then to determine not only the presence or absence of $SO_2$ and $NO_2$ in the stack gas mixture, it is also possible to determine the concentration of the $SO_2$ and the $NO_2$ therein. Further, the sum of NO and $NO_2$ can be determined by converting all the NO to $NO_2$ by turning on switch 304 and supplying ozone (FIG. 18). See equation (1).

The use of the reference filter 33 is required in order to obtain necessary outputs to calculate concentration.

Measuring filter 34 is required to perform the $SO_2$ concentration measurement. Filter 35 is required to obtain the $NO_2$ measurement. Filters 36 and 38 are employed for calibration purposes regarding the $SO_2$ measurement. Filters 37 and 39 are employed for calibration in making the $NO_2$ measurement (or NO plus $NO_2$ as stated previously).

As stated previously, wheel 28 is rotated at a substantially constant velocity by motor 208. Such rotation places filters 34, 38, 35 and 39 in succession in that order approximately in the place where the filter 33 is shown in FIG. 15. Photomultiplier 50 thus "sees" light passing through each filter in succession. Thus, during certain successive periods, the output of the photomultiplier 50 indicates a light intensity corresponding to the respective filters.

The output of sensor 56' in FIG. 6 is directly proportional to the common logarithm of the intensity of the light which, at that instant, is passing through a particular one or two of the filters. See the Vincent et al. U.S. Pat. No. 3,796,887 issued Mar. 12, 1974. The output of sensor 56' is thus, more or less, a time-shared signal. Although the output of sensor 56' is impressed upon all of the sample and hold circuits 57'-61', each sample and hold circuit only samples one-fifth of the total information and at a time corresponding to one particular filter as determined by pickups 42 and 43, and gating circuit 55'. See the said Vincent et al. patent. For example, gating circuit 55' has outputs indicated at a', b', c', d' and e'. Output 9' opens the gate of sample and hold circuit 57' to sample the output of sensor 56' only when filter 33 lies in the path of light along the line 173.

Sample and hold circuit 57' thus corresponds to filter 33. Sample and hold circuits 58', 59', 60' and 61' then correspond to filters 34, 38, 35 and 39, respectively. For the operation of gating circuit 55', see the said Vincent et al. patent.

All calibration and zeroing is done with switch 304 (FIG. 18) off.

For one part of the calibration, switches 102' and 103' are thrown to their dotted line positions. The position of wiper 88' on potentiometer winding 87' is then varied until indicator 123' shows an output voltage equal to zero. The setting of corresponding potentiometer 86" is similarly varied until the indicator 124' shows an output voltage of zero.

If desired, an output voltage adequate to produce a full scale indication on indicators 123' and 124' may be employed to indicate, for example, a concentration of 3.0, where the neutral density filters 36 and 37 each transmit 1/1000 of the light intensity illuminating the same at all wavelengths. Note that there is a correlation to this and that the logarithm of 1000 to the base 10 is 3.0.

An adjustment for span is made by throwing the switches 102' and 103' to their solid line positions. In this case, the resistance of resistor 116' is adjusted until indicator 123' shows full scale. Similarly, the resistance of resistor 119' is varied until indicator 124' shows full scale.

For operation, after the zero and span corrections, the switches 102' and 103' are again thrown to their dotted line positions. Motor 208 remains energized, wheel 28 rotates at a constant angular velocity and indicators 123' and 124' read. In such reading, indicator 123' produces an indication directly proportional to the concentration of $SO_2$ in the mixture of flue gases. Indicator 124' will produce an indication directly proportional to the concentration of $NO_2$ in the flue gases. If a NO to $NO_2$ conversion is desired, worm 305 is turned automatically or manually (periodically) to zero for the current $NO_2$ indication. Switch 304 (FIG. 18) is then turned on and ozone is pumped through tube 300 if an NO plus $NO_2$ indication is desired.

The signals appearing on the switch poles 108' and 109' are subtracted from that appearing at the output of sample and hold circuit 57' because amplifiers 80', 81', 80" and 81" are all inverter amplifiers.

SUMMARY

It is to be noted that the outputs of amplifiers 121' and 122' in FIG. 6 need not be employed to drive a voltmeter or recorder, but may also be employed to drive other devices or not such as, for example, a process controller with, for example, switch 304 (FIG. 18) on.

The word "concentration," as used herein and in the claims, is hereby defined to include, but not be limited to, the percent of a substance in a mixture of substances by volume.

In FIG. 15, a cap 23' prevents light from lamp 23 from reaching photomultiplier 50 except along path 173.

As will be apparent, the upper end of resistor 90' in FIG. 6 is not connect to resistor 78'. Resister 91' is not connected to resistor 84'. The same is true of the corresponding resistors in adders 64'-65'.

What is claimed is:

1. A photometric analyzer comprising: a probe of an approximately uniform cross section throughout its length and adapted to be fixed in position relative to a stack inside thereof, said probe being hollow and elongated, said probe being perforate to allow stack gases to fill the probe interior, said probe having one end adapted to be fixed to said stack and another end opposite said one end; first means fixed relative to said one stack end to shine light through gases including NO and $NO_2$ in said probe in a direction toward said other end thereof; a photosensitive device fixed relative to said probe in a position to receive said light; second means connected from said device to indicate the concentration of $NO_2$; a perforate tube inside said probe; and third means to cause a flow of ozone within said tube.

2. The invention as defined in claim 1, wherein said cylinder has a plurality of longitudinal rows of holes therethrough, a channel covering one of said rows, and means to introduce air under pressure to said channel to purge said cylinder.

3. The invention as defined in claim 1, including means having a light source to shine light toward said first means, said first means being a mirror fixed relative to said probe at said other end thereof.

4. The invention as defined in claim 3, wherein said probe includes first and second transparent windows sealed thereto at said one and other ends thereof, said mirror being sealed in said other probe end on the side of said second window opposite the side thereof on which said first window is located, said photosensitive device being located on one side of said first window opposite the side thereof on which said second window is located, and means to blow air over the sides of said windows which face each other.

5. The invention as defined in claim 3, wherein said probe includes a hollow cylinder adapted to be mounted with its axis horizontal relative to a vertical stack.

6. The invention as defined in claim 5, wherein said probe includes first and second transparent windows sealed thereto at said one and other ends thereof, said mirror being sealed in said other probe end on the side of said second window opposite the side thereof on which said first window is located, said photosensitive device being located on one side of said first window opposite the side thereof on which said second window is located, and means to blow air over the sides of said windows which face each other.

7. The invention as defined in claim 6, wherein said cylinder has a plurality of longitudinal rows of holes therethrough, a channel covering one of said rows, and means to introduce air under pressure to said channel to purge said cylinder.

8. A photometric analyzer comprising: a light tight housing; a member movable relative to said housing inside thereof, said member having at least first and second light filters fixed relative thereto at first and second different positions thereon, respectively; a conduit to convey NO and $NO_2$; first means fixed relative to said housing to shine light through said NO and $NO_2$, and subsequently thereto, to shine light through said first and second filters in succession as said member is moved; second means mounted on said housing to move said member, said first filter having a passband effectively at a first wavelength where $NO_2$ has no substantial absorption, said second filter having a passband effectively at a second wavelength where $NO_2$ does have substantial absorption; a photomultiplier having a logarithmic output fixed relative to said housing inside thereof in a position to receive light from said first means which has passed through said gas mixture and through said filters; first and second circuit means connected from said photomultiplier to sample and hold the photomultiplier output during first and second times that said photomultiplier is illuminated by the passage of light through said first and second filters, respectively, third means connected from all of said circuit means to indicate a first difference in the magnitudes of the output of said photomultiplier at said first and second times, said first difference being directly proportional to the concentration of said $NO_2$; a perforate tube in the path of said NO; and fourth means to pass ozone through said tube.

9. The invention as defined in claim 8, wherein a probe is provided that is adapted to be fixed relative to a stack inside thereof, said probe having first and second ends and a perforate wall therebetween, said first means including a device fixed relative to and at one of said probe ends to direct light toward said photomultiplier, one of said circuit means including an inverter amplifier connected from said photomultiplier to said third means, and fifth means connected to said probe to purge the interior of said probe with air, said amplifier having an adjustable input to set the output of said third means equal to zero while said probe is purged as aforesaid, said tube being located within the interior of said probe.

10. The device as defined in claim 8, wherein said member has a third light filter at a position thereon different from those positions of said first and second light filters, said first means being adapted to shine light through said gas mixture and subsequently thereto through each of said light filters in succession as said member is moved, said third light filter having a passband effectively at said second wavelength, a first neutral density filter fixed relative to said member in the optical path through said third light filter, third circuit means connected from said photomultiplier to sample and hold the output thereof during the time that said photomultiplier is illuminated by the passage of light through said third light filter and said first neutral density filter, and a single-pole, double-throw switch having a pole connected to said third means and a contact connected from the outputs of said second and third circuit means, respectively, said third means including an amplifier with an adjustable gain to calibrate for full scale when said switch connects said third means to said amplifier.

11. The invention as defined in claim 10, wherein said third means includes a D.C. voltmeter connected from the output of said amplifier and calibrated in concentration.

12. The invention as defined in claim 8, wherein said member includes a rotatable wheel, said filters being angularly spaced therearound, said second means including a substantially constant speed motor, and pulse generating means responsive to the position of said wheel and having an output connected to said circuit means to cause the same to sample synchronously when a corresponding filter passes through the field of view of said photomultiplier.

13. The invention as defined in claim 12, wherein a counter and a set of gates are connected from said pulse generating means to each said circuit means to cause each sample over mutually exclusive periods of time.

14. The invention as defined in claim 13, wherein said pulse generating means includes a reset pickup to reset said counter once for each revolution of said wheel.

15. The invention as defined in claim 8, including a third light filter fixed relative to said member at a position thereon different from the positions of said first and second light filter, said first means also being adapted to shine light through said gas mixture and subsequently thereto through each of said filters in succession, said third filter having a passband effectively at third wavelength different from said first and second wavelengths where a predetermined gas has substantial absorption, said predetermined gas having no substantial absorption at said first wavelength, third circuit means connected from said photomultiplier to sample and hold the output thereof during the time that said photomultiplier is illuminated by the passage of light through said third filter, said third means also being connected from said third circuit means and being adapted to indicate a second difference in the magnitudes of the output of said photomultiplier at first and third times that said first and third filters are respectively located in front thereof, said second difference being directly proportional to the concentration of said predetermined gas.

16. The invention as defined in claim 15, wherein said member has fourth and fifth light filters at different positions thereon which are also different from the positions of said first, second and third light filters, said first means being adapted to shine light through said gas mixture and subsequently thereto through each of said light filters in succession as said member is moved, said fourth and fifth light filters having passbands effectively at said second and third wavelengths, respectively, a first neutral density filter fixed relative to said member in the optical path through each of said fourth and fifth light filters, fourth and fifth circuit means connected from said photomultiplier to sample and hold the output thereof during the time that said photomultiplier is illuminated by the passage of light through said fourth and fifth light filters, respectively, and first and second single-pole, double-throw switches each having a pole connected to said third means and a pair of contacts connected from the outputs of said second and fourth, and third and fifth circuit means, respectively, said third means including an amplifier with an adjustable gain to calibrate for full scale when said switches connect said fourth or fifth circuit means to said amplifier.

17. The invention as defined in claim 10, wherein a probe is provided that is adapted to be fixed relative to a stack inside thereof, said probe having first and second ends and a perforate wall therebetween, said first means including a device fixed relative to and at one of said probe ends to direct light toward said photomultiplier, said second and third circuit means respectively including second and third amplifiers connected from the output of said photomultiplier to said third means, and fifth means connected to said probe to purge the interior of said probe with air, said second and third amplifiers having variable inputs to set the output of said third means equal to zero while said probe is purged as aforesaid, said third means having an adjustable gain amplifier.

18. The invention as defined in claim 17, wherein said member has light filters at different positions thereon which are also different from the positions of said first, second and third light filters, said first means being adapted to shine light through said gas mixture, and subsequently thereto, through each of said light filters in succession as said member is moved, said fourth and fifth light filters having passbands effectively at said second and third wavelengths, respectively, a first neutral density filter fixed relative to said member in the optical path through each of said fourth and fifth light filters, fourth and fifth circuit means connected from said photomultiplier to sample and hold the output thereof during the time that said photomultiplier is illuminated by the passage of light through said fourth and fifth light filters, respectively, and first and second single-pole, double-throw switches each having a pole connected to said third means and a pair of contacts connected from the outputs of said second and fourth, and third and fifth circuit means, respectively, said third means including a first auxiliary amplifier with an adjustable gain to calibrate for full scale when said switches connect said fourth or fifth circuit means to said first auxiliary amplifier.

19. The invention as defined in claim 18, wherein said member includes a rotatable wheel, said filters being angularly spaced therearound, said second means including a substantially constant speed motor, and pulse generating means responsive to the position of said wheel and having an output connected to said circuit means to cause the same to sample synchronously when a corresponding filter passes through the field of view of said photomultiplier.

20. The invention as defined in claim 19, wherein said third means includes a D.C. voltmeter for each said difference, said first auxiliary amplifier being connected to one of said voltmeters, and a second auxiliary, adjustable gain amplifier connected to the other of said voltmeters.

21. A photometric analyzer comprising: a light tight housing, a wheel rotatably mounted relative to and inside of said housing; a motor mounted inside said housing, said motor being adapted to rotate an output shaft thereof at a substantially constant angular velocity; a driving connection between said motor drive shaft and said wheel to rotate said wheel at an approximately constant angular velocity about a predetermined axis; first, second, third, fourth and fifth circular light filters having centers lying on a mathematical circular cylinder concentric with the axis of rotation of said wheel; first means fixed relative to said housing to shine light through a mixture of gases, and subsequently thereto, to shine light through said filters, in succession, as said wheel is rotated at a substantially constant velocity; said first filter having a passband effectively at a first wavelength where $NO_2$ has no substantial absorption, said second filter having a passband effectively at a second wavelength where said $NO_2$ does have substantial absorption, said third filter having a passband effectively at a third wavelength where a first predetermined gas does have substantial absorption, said first gas having no substantial absorption at said first wavelength, said fourth filter being substantially identical to said second filter, said fifth filter being substantially identical to said third filter; a photomultiplier having a logarithmic output fixed relative to said housing inside thereof to receive, in succession, the light passed by each of said filters; a first neutral density filter fixed relative to said wheel coextensive with said fourth filter to attenuate the light which passes through said fourth filter and which is intercepted by said photomultiplier; a second neutral density filter fixed relative to said wheel coextensive with said fifth filter to attenuate the light that passes through said fifth filter and is intercepted by said photomultiplier; first, second, third, fourth and fifth sample and hold circuits having first, second, third, fourth and fifth sampling gates, respectively, first, second, third, fourth and fifth storage capacitors, respectively, and first, second, third, fourth and fifth output amplifiers; first, second, third and fourth adjustable input inverter amplifiers connected from said photomultiplier, said first sample and hold circuit being connected from said photomultiplier, said first, second, third, fourth and fifth sampling gates being connected from the outputs of said photomultiplier and said first, second, third and fourth inverter amplifiers, respectively, to the inputs of said first, second, third, fourth and fifth output amplifiers, respectively; a gating circuit having first, second, third, fourth and fifth outputs respectively connected to said first, second, third, fourth and fifth sampling gates to turn the same on and off, but not necessarily in that order, said first, second, third, fourth and fifth sampling gates being opened when light intercepted by said photomultiplier passes through said first, second, third, fourth and fifth filters, respectively, said first, second, third, fourth and fifth capacitors being connected from the outputs of said first, second, third, fourth and fifth sampling gates, respectively, to a point of reference potential; first and second single-pole, double-throw switches, each of said switches having a pole and first and second contacts, the outputs of said second and fourth output amplifiers being connected to the first and second contacts of said first switch, respectively, the outputs of said third and fifth output amplifiers being connected to the first and second contacts of said second switch, respectively; first and second voltage indicators; and first and second analog adders, said first adder being connected from the output of said first sample and hold circuit and from the pole of said first switch to said first and second adder being connected from said first sample and hold circuit and from said second switch pole to said second indicator, each of said adders including an adjustable gain amplifier; a perforate tube contiguous to said gas mixture; and means to cause a flow of ozone in said tube.

* * * * *